United States Patent [19]

Kratz et al.

[11] Patent Number: 5,756,839
[45] Date of Patent: May 26, 1998

[54] PROCESS FOR PREPARING D,L-ASPARTIC ACID FROM AMMONIUM SALTS OF THE MALEIC ACID

[75] Inventors: Detlef Kratz, Heidelberg; Tom Witzel, Ludwigshafen; Rudolf Bäzner, Mannheim; Matthias Kroner, Eisenberg; Uwe Pressler, Waldsee, all of Germany

[73] Assignee: BASF Aktiengesellschaft, Ludwigshafen, Germany

[21] Appl. No.: 809,141

[22] PCT Filed: Sep. 13, 1995

[86] PCT No.: PCT/EP95/03600

§ 371 Date: Mar. 24, 1997

§ 102(e) Date: Mar. 24, 1997

[87] PCT Pub. No.: WO96/09277

PCT Pub. Date: Mar. 28, 1996

[30] Foreign Application Priority Data

Sep. 24, 1994 [DE] Germany ............... 44 34 172.5

[51] Int. Cl.$^6$ ............ C07C 227/00; C07C 229/00; C07C 227/06; C07C 229/24
[52] U.S. Cl. ............................. 562/554; 562/571
[58] Field of Search ............... 435/109; 562/571, 562/554

[56] References Cited

U.S. PATENT DOCUMENTS 4,560,653  12/1985  Sherwin et al. .
4,963,672  10/1990  Merger et al. ............... 540/538
5,541,090   7/1996  Sakano et al. ............... 435/109

FOREIGN PATENT DOCUMENTS 2 029 502   12/1971   Germany .
126 075      3/1980   Germany .
40-25133     2/1965   Japan .
7-247251     9/1995   Japan .

OTHER PUBLICATIONS

Derwent Orbit Abstract 77–57662y/33 Abs DD–126075 (Jun. 15, 1977) Berlin Chemie Veb.

Derwent Orbit Abstract 77–01621T/02 Abs DE 2029502 (Feb. 1972) Lentia GmbH Chem.

Aps Abstract Japan 07–247251 (Sep. 26, 1996) Fujii et al.

*Primary Examiner*—Herbert J. Lilling
*Attorney, Agent, or Firm*—Oblon, Spivak, McClelland, Maier & Neustadt, P.C.

[57] ABSTRACT

A process is disclosed for preparing D,L-aspartic acid by heating aqueous solutions of ammonium salts of the maleic acid. The molar ratio of maleic acid to ammonia ranges from 1:1 to 1:50. The process is carried out at temperatures from 60° to 250° C. and pressures of at least 1 bar. The pressure applied during the reaction is adjusted to ensure that the reaction mixture is almost completely present in liquid phase. Excess ammonia is removed and the reaction solution is acidified so as to release D,L-aspartic acid, which is then isolated.

7 Claims, No Drawings

PROCESS FOR PREPARING D,L-ASPARTIC ACID FROM AMMONIUM SALTS OF THE MALEIC ACID

BACKGROUND OF THE INVENTION

The invention relates to a process for preparing D,L-aspartic acid by heating aqueous solutions of ammonium salts of maleic acid at elevated temperatures under pressure, acidifying the reaction solution to liberate D,L-aspartic acid and isolating the D,L-aspartic acid.

DISCUSSION OF THE BACKGROUND

DE-A-2 029 502 discloses the preparation of D,L-aspartic acid by heating aqueous solutions of the diammonium salt of maleic acid at from 110° to 145° C. under from 2 to 5 bar. The aqueous solution of the diammonium salt of maleic acid is prepared by neutralizing an aqueous solution of maleic acid with aqueous ammonia at not above 20° C., the pH of the ammonium salt solution being 7.5. The reaction solution obtainable in this way is acidified with strong mineral acids, such as hydrochloric acid, until the pH is 3 in order to liberate the aspartic acid from the monoammonium salt which is initially formed. According to the example in the application, the yield of D,L-aspartic acid after recrystallization from water is 61% of theory. However, the space-time yields are unsatisfactory.

D,L-aspartic acid is prepared by the process disclosed in DD-A-126 075 by preparing the diammonium salt of maleic acid in a conventional way by neutralizing maleic anhydride with aqueous ammonia, evaporating it under atmospheric pressure up to 115° C., adding a carboxamide as catalyst and further evaporating the resulting aqueous solution under atmospheric pressure up to 120–130° C., and stirring the reaction mixture at this temperature for 16 hours. It is then cooled to 80° C., hydrochloric acid is added, and the mixture is refluxed in order to destroy the catalyst. The excess hydrochloric acid is then distilled off under reduced pressure, the residue is taken up in water, and the aspartic acid is precipitated by adjusting the solution to pH 2.8. The yield of D,L-aspartic acid after recrystallization is 63%.

JP-A-25 133/65 discloses the preparation of D,L-aspartic acid by reacting maleic acid with ammonia in the presence of ammonium compounds such as ammonium chloride or ammonium acetate. The aspartic acid is liberated from its ammonium salt by adding maleic acid to the reaction solution. This entails adjustment of the pH to 2.5–3. The D,L-aspartic acid which results in crystalline form is filtered off with suction, and the mother liquor, which contains ammonium maleate, is reused.

U.S. Pat. No. 4,560,653 discloses the preparation of L-aspartic acid by enzymatic addition of ammonia onto fumaric acid. L-aspartic acid is precipitated from the resulting ammonium L-aspartate solution by adding maleic acid. The mother-liquor remaining after removal of L-aspartic acid is subjected to an isomerization step in which maleic acid is converted into fumaric acid, subsequently purified and then recycled to the enzymatic addition.

SUMMARY OF THE INVENTION

It is an object of the present invention to provide a process for preparing D,L-aspartic acid which provides higher yields of D,L-aspartic acid than known processes.

We have found that this object is achieved by a process for preparing D,L-aspartic acid by heating aqueous solutions of ammonium salts of aspartic acid at elevated temperatures under pressure, acidifying the reaction solution to liberate D,L-aspartic acid and isolating the D,L-aspartic acid, when maleic acid and ammonia are reacted in a molar ratio of from 1:2.1 to 1:50 in aqueous solution at from 60° C. to 250° C. under pressures of at least 1 bar, the pressure being controlled during the reaction in such a way that the reaction mixture is almost entirely in the liquid phase.

DETAILED DESCRIPTION OF THE PREFERRED EMBODIMENTS

In contrast to the prior art processes, in the process according to the invention the reaction of ammonium salts of maleic acid in aqueous solution is carried out in such a way that the reaction solution is virtually quantitatively in the condensed phase under the reaction conditions. This ensures that the concentration of ammonia available for reaction with maleic acid in the solution is maximized.

The process according to the invention can be carried out continuously or batchwise. The solutions of ammonium salts of maleic acid are prepared in a known manner. The starting material can be maleic acid or maleic anhydride, which is known to be hydrolyzed to maleic acid in water. Maleic acid is preferably neutralized with ammonia in aqueous solution. The procedure for this can be such that a solution of ammonia in water, preferably using concentrated ammonia, is combined with an aqueous solution of maleic acid. However, it is also possible to pass gaseous ammonia into an aqueous solution of maleic acid. Maleic acid and ammonia are employed in the process according to the invention in a molar ratio of from 1:2.1 to 1:50, preferably 1:2.1 to 1:10. Based on the maleic acid content, the concentration of ammonium maleate in the aqueous solutions is from 5 to 40, preferably 10 to 30, % by weight. The aqueous solution of the ammonium salts of maleic acid preferably contains an excess of ammonia. The aqueous solutions which are particularly preferably employed have a maleic acid : ammonia molar ratio of from 1:3 to 1:7. The pH of the aqueous solutions of ammonium maleate is, for example, in the range from 7.5 to 11.5, preferably 8.5 to 11.

The aqueous solutions of the ammonium salts of maleic acid are reacted in a pressure vessel under a pressure of at least 1 bar. Examples of suitable pressure vessels are autoclaves or tubular reactors. It is also possible for autoclaves and tubular reactors to be connected in series or else for the reaction to be carried out continuously in a cascade of 2 or 3 to 4 autoclaves equipped with a stirrer. The reaction can also be carried out by subsequently metering ammonia in during the course of the reaction. The pressure vessels are, according to the invention, completely filled with the aqueous solution of the ammonium salts of maleic acid so that virtually no gas space is available above the liquid. In practice, the aqueous solutions are pumped into the pressure vessel until the pressure has reached that under which the reaction is to take place. This pressure is at least 1 bar and is normally in the range from 2 to 100 bar. However, higher pressures can also be used, but this signifies virtually no advantage for the yield and conversion to D,L-aspartic acid. Operation under very high pressures requires appropriate design of apparatus so that, for cost reasons, the process according to the invention will rather be carried out under lower pressures, eg. in the range from 2 to 90, preferably 5 to 80 and, in particular, 10 to 40, bar. The reaction can also be carried out virtually completely in the liquid phase by controlling the pressure for a given amount of solution by injecting an inert gas, for example nitrogen. The solution may, where appropriate, contain inert solvents such as ethers, eg. dioxane, tetrahydrofuran, diisopropyl ether, methyl tert-butyl ether or hydrocarbons such as toluene, xylene, octane or decane. It is additionally possible to use N-methylpyrrolidone as solvent. If the aqueous solution of the ammonium salts of maleic acid contains an inert solvent differing from water, the amounts of inert solvent are, for example, 1 to 50% by weight, based on the total amount of solvent.

D,L-aspartic acid is obtained by heating the aqueous solutions of ammonium salts of maleic acids at temperatures in the region of, for example, 60 to 250, preferably 100° to 200, ° C. The reaction may, where appropriate, be carried out in the presence of a heterogeneous catalyst. Suitable heterogeneous catalysts which dissolve neither in the initial solution of the ammonium salts nor in the reaction mixture are, for example, aluminum oxide, silicon dioxide, titanium dioxide, magnesium oxide, zinc oxide and mixed oxides such as spinnel types, titanium tungsten oxides, tin/aluminum oxides or such catalysts which are doped, for example, with transition metals of subgroups 1 to 8 of the Periodic Table, and zirconium dioxide. These carrier materials can, where appropriate, be doped with alkaline components such as alkali metal or alkaline earth metal oxides or acidic additives, eg. phosphoric acid. Ion exchangers with acidic or basic groups are additionally suitable as catalyst. The ion exchangers are crosslinked polymers which are insoluble in the aqueous reaction media employed according to the invention.

The residence time of the reaction solution in the pressure reactor is, for example, from 1 to 300, preferably 15 to 120, minutes. The residence time essentially depends on the reaction temperature chosen in each case. Shorter residence times are required at higher temperatures. The reaction solution emerging from the reactor is decompressed and condensed. It contains up to 85% aspartic acid in the form of the ammonium salt, and additional components such as fumaric acid, iminodisuccinic acid, malic acid and small amounts of amides such as asparagine too. If an excess of ammonia based on maleic acid is used, liberation of the D,L-aspartic acid with acids, preferably maleic acid, is preceded by removing excess ammonia from the aqueous reaction solution by distillation. The ammonia distillation can be carried out under atmospheric, elevated or else reduced pressure, eg. in the range from 1 mbar to 50 bar. The mixture of water and ammonia obtained as low boilers can be reused for preparing D,L-aspartic acid by using it to neutralize maleic acid with ammonia in a molar ratio as required according to the invention. The removal of excess ammonia usually entails concentration of the reaction solution. The solids content of the reaction solution is then about 10 to 50, preferably 20 to 40, % by weight. After removal of excess ammonia, the reaction solution has a pH of, for example, 4.7 to 6.5, preferably 5.2 to 6.0. The main constituent of the aqueous solution, comprising at least 15% by weight, is the ammonium salt of aspartic acid. The reaction mixture additionally contains ammonium salts of the other acids mentioned above produced as byproduct in the reaction.

In the preferred embodiment of the process according to the invention, the reaction of the ammonium salts of maleic acid is carried out at from 120° to 180° C., excess ammonia is removed from the reaction solution, the reaction solution is then acidified by adding maleic acid or maleic anhydride, the D,L-aspartic acid is separated from the mother liquor obtainable in this way, and the mother liquor and the excess ammonia are returned, for preparing ammonium salts of maleic acid, to the process for preparing D,L-aspartic acid.

The reaction solution can also in principle be acidified with mineral acids such as sulfuric acid or hydrochloric acid or other acids such as para-toluenesulfonic acid, but the ammonium salts which are then produced cannot be returned to the process. This is why acidification of the reaction solution with maleic acid or maleic anhydride to liberate D,L-aspartic acid is preferred.

If sulfuric acid or hydrochloric acid is used to acidify the reaction solution, it is acidified in a manner known from the literature until the pH is 2.5 to 3, and aspartic acid is removed by conventional methods such as filtration or centrifugation. It is possible in this way to isolate about 90% of the aspartic acid based on the aspartic acid content in the reaction solution. Under these conditions, fumaric acid and iminodisuccinic acid remain in solution. The disadvantage of this isolation method is that it is associated with a loss of at least 10% of the aspartic acid, because the fumaric acid or iminodisuccinic acid still remaining in the solution cannot be utilized and that an inorganic ammonium salt is produced in equimolar amounts.

The reaction solution is acidified with maleic acid, which can be either in solid form or as aqueous solution which can, for example, also be prepared by hydrolyzing maleic anhydride, to adjust the pH of the solution to about 3. It is possible in this way likewise to precipitate about 90% of the aspartic acid from the reaction solution. However, it is necessary where appropriate to add a stoichiometric excess, based on precipitated D,L-aspartic acid, of maleic acid to the reaction solution. The pH is adjusted to from 3.5 to 5, depending on the precipitation conditions, because then the added amount of maleic acid is equivalent to the amount of aspartic acid obtained. This method for precipitating D,L-aspartic acid from the reaction solution is particularly suitable when the mother liquor obtained from the isolation of aspartic acid is returned to the process for renewed preparation of D,L-aspartic acid. The volume present in circulation thus remains constant.

The mother liquor resulting after removal and washing of D,L-aspartic acid mainly contains aspartic acid, maleic acid, fumaric acid and iminodisuccinic acid. The washing water likewise contains the abovementioned acids. The mother liquor and the washing water can be employed according to the invention, after reaction with ammonia, for preparing D,L-aspartic acid, employing said acids with ammonia preferably in a molar ratio of from 1:2.1 to 1:10. Surprisingly, the reaction solution obtained on renewed reaction by the process according to the invention corresponds, in respect to organic constituents, to the direct reaction of ammonium salts of maleic acid by the process according to the invention. Thus, it is possible, by neutralizing the reaction solution with maleic acid and returning the mother liquor to the process, to obtain D,L-aspartic acid without production of inorganic salts and, at the same time, to utilize the byproducts which are produced alongside D,L-aspartic acid, such as fumaric acid, malic acid iminodisuccinic acid, quantitatively for preparing D,L-aspartic acid. Repetition several times of the workup steps and return of the mother liquor and of excess ammonia and renewed precipitation with maleic acid achieves a yield of more than 98% D,L-aspartic acid based on maleic acid.

It is particularly preferred to carry out the process according to the invention continuously, in which case, for example, a recycled mother liquor with recycled ammonia and addition of fresh ammonia and, where appropriate, fresh maleic acid and aqueous solution of ammonium salts of maleic acid is prepared in the intended ratio and reacted in a reactor at from 60° to 250° C. under pressures of at least 1 bar, the pressure being controlled during the reaction in such a way that the reaction mixture is almost completely in liquid phase. The resulting ammonium aspartate solution is freed of excess ammonia and, at the same time, concentrated. The aqueous ammonia obtained is recycled. However, the aqueous ammonia can also be fractionated to obtain concentrated ammonia and water. Both substances can be recycled, employing water to prepare an aqueous solution of maleic acid or for washing aspartic acid. After the removal of excess ammonia, an aqueous solution of maleic acid is added to the reaction solution, adjusting the pH to the range from 3.5 to 5 so that D,L-aspartic acid precipiates. The precipitated D,L-aspartic acid is separated off and washed with water. The mother liquor and the washing water are returned to the process after adding ammonia. The D,L-aspartic acid can be recrystallized where appropriate.

D,L-aspartic acid can be condensed, for example, thermally by heating above 190° C. or in the presence of acids such as phosphoric acid or of acidic ammonium salts such as ammonium bisulfate at, for example, from 170° to 230° C. to give polyaspartimides or to give mixtures of polyaspartimides and polyaspartic acid. The polycondensates are used as detergent additive, for example in amounts of from 1 to 10% by weight, based on the formulation.

The percentage data in the examples mean percent by weight. The compositions of the reaction solutions indicated in the examples were determined by gas chromatography (percentage area).

EXAMPLE 1

An ammonium maleate solution is initially prepared by mixing 120 g of maleic acid, 37 g of ammonia and 243 g of water. The maleic acid content in the solution calculated from this is 30%. The maleic acid : ammonia molar ratio is 1:2.1, and the pH of the ammonium maleate solution is 8.5. The solution is continuously pumped at a delivery rate of 133 ml/h into a tubular reactor which is controlled at a temperature of 160° C. and has a length of 30 m, a diameter of 2 mm and a volume of 100 ml. The pressure in the tubular reactor is controlled by means of a pressure-maintenance system so that the reaction mixture is virtually completely in the form of a liquid phase. The pressure is 80 bar. The discharge from the reactor is condensed and analyzed. The conversion based on maleic acid is 99.9%. The reaction mixture had the following composition:

0.1% maleic acid
4% fumaric acid
79% D,L-aspartic acid
15% iminodisuccinic acid
0.2% maleic acid
0.6% asparagine and
1.1% unidentified compounds.

The reaction mixture is adjusted to pH 3.8 by adding maleic acid. D,L-aspartic acid crystallizes out.

EXAMPLE 2

Firstly a mixture of
69% maleic acid
9% fumaric acid
9% D,L-aspartic acid and
13% iminodisuccinic acid is prepared and converted into a 20% by weight aqueous solution which is then adjusted to pH 8.5 by adding ammonia. This solution is then passed through the reactor indicated in Example 1 under the conditions likewise described therein. The composition of the reaction mixture almost corresponds to the composition of the reaction mixture in Example 1, in particular the reaction solution contains 0.1% maleic acid
4.5% fumaric acid
77% D,L-aspartic acid
15% iminodisuccinic acid and
3.4% unidentified constituents.

EXAMPLE 3

A 20% strength aqueous solution is prepared by mixing 1 mol of maleic acid, water and 2.1 mol of ammonia. The solution is subsequently pumped continuously at a delivery rate of 24 ml/h through a tube which has a length of 30 cm, a diameter of 1.5 cm and a volume of 60 ml. The tube is packed with glass beads which have a diameter of 3 to 5 mm. The tube is heated to 180° C. An overflow device is used to adjust the pressure to 80 bar. The reaction mixture is almost completely in the form of a liquid phase during the reaction at 1800 under 80 bar. The discharge from the reactor is condensed and analyzed. The conversion is 99.4%. The composition of the reaction mixture is 0.6% maleic acid
7.5% fumaric acid
72% D,L-aspartic acid
16% iminodisuccinic acid
1.1% malic acid
2.8% unidentified constituents.

D,L-aspartic acid is precipitated in the form of crystals from the reaction mixture by adding maleic acid to pH 4.7.

EXAMPLE 4

Example 1 is repeated with the sole exception that the reactor temperature is 180° C. The resulting reaction mixture then contains 0.1% maleic acid
3% fumaric acid
83% D,L-aspartic aced
7% iminodisuccinic acid
0.5% malic acid
0.5% L-asparagine and
5.9% unidentified constituents.

D,L-aspartic acid is precipitated by adding maleic acid to the reaction solution until the pH is 4.5.

EXAMPLE 5

Example 1 is repeated with the sole exception that the reactor temperature is increased to 200° C. The reaction mixture has the following composition:

0.5% maleic acid
4% fumaric acid
78% D,L-aspartic acid
6% iminodisuccinic acid
1.4% malic acid
2.5% L-asparagine and
7.6% unidentified constituents.

Addition of maleic acid to the reaction solution until the pH is 4.2 precipitates D,L-aspartic acid.

EXAMPLE 6

Example 3 is repeated with the only difference that the maleic acid : ammonia ratio is 1:3. The reaction solution then contains 0.5% maleic acid 4.5% fumaric acid 80% D,L-aspartic acid 8% iminodisuccinic acid 0.7% malic acid 6.3% unidentified constituents.

D,L-aspartic acid is precipitated by adding maleic acid to the reaction solution until the pH is 4.7.

EXAMPLE 7

Example 3 is repeated with the exceptions that the maleic acid : ammonia ratio is now set at 1:5 and the reaction is carried out at 160° C. The resulting reaction mixture then contains 0.4% maleic acid 4% fumaric acid 83% D,L-aspartic acid 4% iminodisuccinic acid and 8.6% unidentified substances.

EXAMPLE 8

Example 3 is repeated with the exceptions that 1.5 mm alumina pellets are used in place of glass beads as catalyst, and the feed rate is adjusted to 60 ml/h. The reaction solution leaving the reactor has the following composition:

0.1% maleic acid 4.4% fumaric acid

89% D,L-aspartic acid

1% iminodisuccinic acid 2.5% malic acid and

3% unidentified contents.

D,L-aspartic acid is precipitated by adding maleic acid to the reaction solution until the pH is 4.0.

EXAMPLE 9

3000 ml of a 20% strength aqueous solution of 600 g (5.17 mol) of maleic acid neutralized with 264 g (15.51 mol) of ammonia are pumped through the reactor tube described in Example 1, which is kept at 160° C., otherwise under the conditions indicated therein. The reaction mixture leaving the reactor contains 0.4% maleic acid 5% fumaric acid 84% D,L-aspartic acid 8% iminodisuccinic acid and 2.6% unidentified substances.

The pH of the feed is 10.5 and that of the condensed reaction mixture is 9.8.

The excess ammonia is distilled out of the reaction solution and subsequently maleic acid is added until the pH of the solution is 4.3, whereupon D,L-aspartic acid precipitates. The mother liquor and the ammonia which has been distilled off can be employed together with fresh ammonium maleate for synthesizing D,L-aspartic acid, cf. Examples 10 to 12.

EXAMPLE 10

3000 ml of the discharge from the reaction in Example 9 are introduced into a distillation apparatus. 1432 ml of a mixture of water and ammonia are distilled out at the bottom temperature of 100° C. under atmospheric pressure. At the end of the distillation, the pH of the bottom product is 5.85, and it contains 0.4% maleic acid 7% fumaric acid 81% D,L-aspartic acid and 9% iminodisuccinic acid.

The remainder consists of unidentified substances.

EXAMPLE 11

A total of 348 g (3 mol) of maleic acid is added in portions to the bottom product from Example 10 at 20° C. The pH of the solution briefly falls to about 4 during this but then rises as soon as D,L-aspartic acid beings to precipitate. The mixture is stirred at 20° C. for 8 hours, the pH eventually being 4.75. The precipitate is then filtered off with suction and washed with 1000 ml of water. Drying results in 427 g (3.21 mol) of D,L-aspartic acid, corresponding to a yield of 62% based on the amount of maleic acid employed in Example 9.

EXAMPLE 12

The mother liquor and the washing water from Example 11 are combined. Then water and ammonia are added until 2780 ml of a 20% strength aqueous solution with a pH of 10.5 are obtained. This solution is reacted as described in Example 9 and subsequently concentrated as in Example 10. 1453 ml of a bottom product remain. D,L-aspartic acid is then precipitated as described in Example 11 by adding 323 g (2.78 mol) of maleic acid. Drying results in 382 g (2.87 mol) of D,L-aspartic acid, corresponding to a yield of 95.7% based on the amount of maleic acid added in Example 11.

EXAMPLE 13

Example 3 is repeated with the exceptions that the reactor contains no glass beads and the pressure is 15 bar. The composition of the reaction mixture virtually corresponds to the reaction mixture composition indicated in Example 3.

We claim:

1. A process for preparing D,L-aspartic acid by heating aqueous solutions of ammonium salts of maleic acid at elevated temperatures under pressure, acidifying the reaction solution to liberate D,L-aspartic acid and isolating the D,L-aspartic acid, wherein maleic acid and ammonia are reacted in a molar ratio of from 1:2.1 to 1:50 in aqueous solution at from 60° C. to 250° C. under pressures of at least 1 bar, the pressure being controlled during the reaction in such a way that the reaction mixture is almost entirely in the liquid phase.

2. A process as claimed in claim 1, wherein maleic acid and ammonia are employed in a molar ratio of from 1:3 to 1:7.

3. A process as claimed in claim 1, wherein the reaction is carried out in a tubular reactor.

4. A process as claimed in claim 1, wherein the concentration of ammonium maleate based on maleic acid in the aqueous solutions is from 5 to 40% by weight.

5. A process as claimed in claims 1, wherein the reaction is carried out at from 120° to 180° C. under from 2 to 40 bar.

6. A process as claimed in claim 1, wherein excess ammonia is removed from the reaction solution, the reaction solution then is acidified by adding maleic acid or maleic anhydride, D,L-aspartic acid is separated from the mother liquor obtainable in this way, and the mother liquor and the excess ammonia are returned, to the process for preparing D,L-aspartic acid.

7. A process as claimed in claims 1, which is carried out continuously.

* * * * *